US009144535B1

(12) United States Patent
Daly et al.

(10) Patent No.: US 9,144,535 B1
(45) Date of Patent: Sep. 29, 2015

(54) PARTICULATE ZINC OXIDE WITH MANGANESE ION DOPANT

(71) Applicant: JOHNSON & JOHNSON CONSUMER INC., Skillman, NJ (US)

(72) Inventors: Susan Daly, Basking Ridge, NJ (US); Euen Thomas Graham Ekman Gunn, Hopewell, NJ (US); Prithwiraj Maitra, Hillsborough, NJ (US); Eduardo Colla Ruvolo, Jr., Plainsboro, NJ (US); Yongyi Zhang, Harrison, NJ (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 5 days.

(21) Appl. No.: 14/269,407

(22) Filed: May 5, 2014

(51) Int. Cl.
*H01L 29/12* (2006.01)
*A61K 8/27* (2006.01)
*A61Q 17/04* (2006.01)

(52) U.S. Cl.
CPC . *A61K 8/27* (2013.01); *A61Q 17/04* (2013.01); *A61K 2800/26* (2013.01)

(58) Field of Classification Search
CPC ............ H01L 21/31641; H01L 21/0257; H01L 21/31658; H01L 21/02348; H01L 21/0231; H01L 21/52105; H01L 21/02178; H01L 21/28079; H01L 23/53219; H01L 29/24; H01L 29/106; H01L 29/207; H01L 29/7869
USPC .......... 257/43, 148, 749, 219, 249, 310, 607, 257/742, E21.006, E21.043, E21.077, 257/E21.121, E21.126, E21.127, E21.134, 257/E21.253, E21.329
See application file for complete search history.

(56) References Cited

U.S. PATENT DOCUMENTS

| 5,198,025 | A | 3/1993 | Dausch |
|---|---|---|---|
| 5,441,726 | A | 8/1995 | Mitchnick et al. |
| 5,800,824 | A * | 9/1998 | Pfrommer et al. ............ 424/401 |
| 8,753,684 | B2 * | 6/2014 | Pfluecker et al. ............ 424/489 |
| 2006/0104925 | A1 | 5/2006 | Knowland et al. |
| 2006/0134026 | A1 | 6/2006 | Park et al. |
| 2006/0239941 | A1 * | 10/2006 | Park et al. ....................... 424/59 |
| 2008/0031832 | A1 | 2/2008 | Wakefield et al. |
| 2012/0258154 | A1 | 10/2012 | Pfluecker et al. |

FOREIGN PATENT DOCUMENTS

WO WO 2006/058209 A 6/2006
WO WO 2006/061627 A 6/2006

OTHER PUBLICATIONS

Aydin et al., "Synthesis, diffused reflectance and electrical properties of nanocrystalline Fe-doped ZnO via sol-gel calcination technique", *Optics & Laser Technology* (2013) 48:447-452.
Feng et al., "Hydrothermal synthesis and photocatalytic performance of metial-ions doped $TiO_2$", *Applied Catalysis A: General* 413-414 (2012) 238-244.
Truffault et al., "Synthesis of nano-hematite for possible use in sunscreens", *Journal of Nanoscience and Nanotechnology* (Mar. 2011) 11(3):2413-20.
Truffault et al., "Synthesis and characterization of Fe doped $CeO_2$ nanoparticles for pigmented ultraviolet filter applications", Journal of Nanoscience and Nanotechnology (May 2011) 11(5):4019-28.

* cited by examiner

*Primary Examiner* — David Nhu

(57) ABSTRACT

A particulate metal oxide is provided that includes a cationic portion containing a zinc portion, a first manganese dopant portion and a second dopant portion selected from the group consisting of iron and aluminum, wherein the zinc portion is about 99% by weight or more of the cationic portion and the manganese dopant portion and second dopant portion are present in a weight ratio of from about 5:1 to 1:5.

13 Claims, No Drawings

PARTICULATE ZINC OXIDE WITH MANGANESE ION DOPANT

FIELD OF THE INVENTION

The invention relates to particulate zinc oxide. More specifically, the invention relates to particulate zinc oxide that is doped with manganese and a second dopant.

BACKGROUND OF THE INVENTION

Skin cancer is a significant public health concern which represents 50% of diagnosed cases of cancer in the United States. Ultraviolet radiation (UV) can cause molecular and cellular level damage, and is considered the leading environmental factor responsible for skin cancer. The prolonged exposure to UV radiation, such as from the sun, can lead to the formation of light dermatoses and erythemas, as well as increase the risk of skin cancers, such as melanoma, and accelerate skin aging processes, such as loss of skin elasticity and wrinkling.

The damaging effects of UV exposure can be suppressed by topical application of sunscreens which contain compounds that absorb, reflect or scatter UV, typically in the UVA (wavelengths from about 320 to 400 nm) or UVB (wavelengths from around 290 to 320 nm) range of the spectrum. Numerous sunscreen compounds are commercially available with varying ability to shield the body from ultraviolet light.

Zinc oxide is a particulate material that is useful as a sunscreen, since it absorbs and scatters ultraviolet radiation. However, the inventors have recognized that a need exists for zinc oxide having enhanced optical properties, particularly for use in sunscreens and personal care products, more particularly for enhanced UVA absorption.

SUMMARY OF THE INVENTION

According to one aspect of the invention, a particulate metal oxide comprising a cationic portion is provided. The cationic portion comprises about 99% by weight or more of a zinc portion, a first manganese dopant portion and a second dopant portion selected from the group consisting of iron and aluminum. The particulate metal oxide has a Long-Short Absorbance Ratio that is greater than a Long-Short Absorbance Ratio of a comparable particulate metal oxide, as defined herein. The manganese dopant portion and the second dopant portion may be present in a weight ratio from about 5:1 to about 1:5, or about 4:1 to about 1:4, or from about 1:3 to about 3:1.

DETAILED DESCRIPTION OF THE INVENTION

The inventors have found that a particulate zinc oxide having certain cationic dopants that are present in relatively low levels and in particular ratios provides improved absorption in the UVA portion of the electromagnetic spectrum over a comparable particulate zinc oxide, as defined herein.

It is believed that one skilled in the art can, based upon the description herein, utilize the present invention to its fullest extent. The following specific embodiments are to be construed as merely illustrative, and not limitative of the remainder of the disclosure in any way whatsoever. Unless defined otherwise, all technical and scientific terms used herein have the same meaning as commonly understood by one of ordinary skill in the art to which the invention belongs. Unless defined otherwise, all references to percent are percent by weight.

Particulate Zinc Oxide

Embodiments of the invention relate to particulate metal oxides. By "particulate" it is meant a material that is, under ambient conditions, a finely-divided, solid material. As one skilled in the art will readily recognize, metal oxides are ionic solids, generally comprising predominantly metal cations and anions comprising predominantly oxygen anions arranged in a crystalline lattice structure.

Accordingly, particulate metal oxides of the present invention comprise a cationic portion. The cationic portion comprises about 99% by weight or more of a zinc portion. According to certain embodiments, the zinc portion is about 99% to about 99.75% of the cationic portion, such as from about 99% to about 99.5%, such as from about 99% to about 99.25%.

The cationic portion further comprises a first manganese dopant portion and a second dopant portion selected from the group consisting of iron and aluminum. As used herein, "dopant", or "dopant portion" means those cations, or portion of cations, that are intimately incorporated into the crystalline lattice structure of the metal oxide, as further described herein, thereby modifying the electronic properties of the metal oxide. One skilled in the art will recognize that the mere coating of a particulate metal oxide with a material having metal cations is not sufficient in and of itself to provide modified electronic properties of the metal oxide, since mere coating will not provide intimate incorporation of the metal cations into the crystalline lattice structure of the metal oxide.

In addition to the zinc portion, the cationic portion further comprises a first manganese dopant portion. The manganese portion may be about 0.1% to about 0.75% by weight of the cationic portion. According to certain embodiments, the manganese dopant portion is about 0.15% to about 0.8% of the cationic portion, such as from about 0.25% to about 0.75%. The manganese dopant portion may exist in varying oxidation states. According to one embodiment the manganese exists as either $Mn^{2+}$ or $Mn^{3+}$. In another embodiment, the manganese exists as $Mn^{2+}$.

The cationic portion further comprises a second dopant portion that is selected from the group consisting of iron and aluminum. That is, in one embodiment the second cationic dopant portion may consist of iron. In a second embodiment the second cationic dopant portion may consist of aluminum. In a third embodiment the second cationic dopant portion may comprise a combination of iron and aluminum. The iron may exist in varying oxidation states. According to one embodiment the iron exists as either $Fe^{2+}$ or $Fe^{3+}$. In another embodiment, the iron exists as $Fe^{2+}$. Similarly, the aluminum may exist in varying oxidation states. According to one embodiment the aluminum exists as $Al^{3+}$.

Similarly to the manganese dopant portion, the second dopant portion may be about 0.1% to about 0.75% by weight of the cationic portion. According to certain embodiments, the second dopant portion is about 0.15% to about 0.8% of the cationic portion, such as from about 0.25% to about 0.75%.

The sum of the manganese dopant portion and the second dopant portion may be from about 0.25% to about 1% of the cationic portion, such as from about 0.5% to about 1% of the cationic portion, such as from about 0.75%, to about 1% of the cationic portion, such as from about 0.85% to about 0.99% of the cationic portion.

According to certain embodiments, the inventors have found when the manganese portion and the third portion are present in a particular weight ratio of manganese portion: third portion, that is from about 1.5 to 5:1, or 1:3 to 3:1, (inclusive of endpoints), particular benefits are achieved in UVA absorption. For example, the weight ratio of manganese portion: third portion may be 1:3, 1:1, or 3:1, among other ratios within the above range. By way of more specific examples, the cationic portion may be about 0.25% of manganese portion and 0.75% third portion; or 0.5% manganese portion and 0.5% third portion; or about 0.75% manganese portion and 0.25% third portion.

As one skilled in the art will readily appreciate, additional metal cations may be present in small concentrations in the particulate metal oxide without compromising the properties thereof. For example, in certain embodiments, small concentrations of these additional cations may be collectively present in the cationic portion in concentrations of, for example, less than about 0.5%, such as less than about 0.25%, such as less than about 0.1%. According to certain embodiments, the additional cations may be collectively present in the cationic portion in a concentration from about 0.001% to about 0.25%, such as from about 0.001% to about 0.1%. The additional cations may include cations of alkali metals, alkaline earth metals; transition metals other than zinc, manganese and iron; as well as cations of metals such as gallium, germanium, gallium, indium, tin, antimony, thallium, lead, bismuth, and polonium.

Particulate metal oxides of the present invention may be made by various methods, such as methods reducing oxide ores using, for example, carbon or other suitable reducing agents, and then re-oxidizing. Other suitable methods include wet chemical methods. One example of a wet chemical method includes mixing alkaline salt solutions of the various cations and causing ZnO to precipitate by reducing the pH using an acid such as oxalic or formic acid. A particularly suitable wet chemical method is the so-called "sol-gel" method, an example of which is described below.

According to one embodiment of the invention, the particulate metal oxide formed by a method that includes combining a solvent system comprising water with a zinc salt, a manganese salt, and a third salt (e.g., an iron salt, an aluminum salt or combinations thereof). According to certain embodiments, the ratio of manganese cation to third salt cation is from 1:3 to about 3:1.

Any of a variety of salts may be used as sources of the various cations. Examples include zinc acetate, zinc chloride, manganese chloride, manganese sulfate, manganese acetate, ferric chloride, ferric sulfate, and aluminum chloride, among other salts. Additional components may be added to the mixture of the solvent system and the salts. For example, a surfactant such as an ethanolamine (e.g. triethanolamine) as well as homogenizing and or pH adjusting agents such an alcohol and ammonia may be added as well. Suitable alcohols include ethanol, 2-methoxyethanol, and the like. Typically in a sol-gel process, a stable, colloidal solution (sol) is formed after mixing the solvent system, the salts and the optional surfactant, and homogenizing/pH adjusting agents. Over time, a gel network comprising zinc cations, manganese cations and cations of the third salt is then gradually formed, by solidification and condensation of colloidal particles having solvent system trapped therein.

The gel network is then allowed to dry, such as at ambient temperatures, to remove at least portions of the solvent system. The dried gel network is then calcined, heated at high temperatures in an oxygen-containing atmosphere, to remove any remaining solvent system and/or residual organics and to densify the gel network. Upon sufficient heating, the particulate metal oxide is formed. According to certain embodiments, the calcination is performed at a temperature of at least about 400° C., such as from about 400° C. to about 1200° C., such as from about 600° C. to about 1000° C., such as about 700° C.

According to certain embodiments, the particulate metal oxides of the present invention are characterized by surprisingly high Long-Short Absorbance Ratios (LSAR). "LSAR" is a measure of the relative amount of absorbance in the long wavelength UVA-I and visible region of the spectrum, which is the region of the spectrum that is typically absorbed less by conventional sunscreens, yet is still responsible for biological deleterious effects, as compared with short wavelength absorbance. This ratio of absorbance across long wavelengths to absorbance at shorter wavelengths thus provides a basis for comparing the ability of the various doped particulate metal oxides to absorb in this region of the spectrum. Long-Short Absorbance Ratio may be determined by integrating (summing) the absorbance from wavelengths ranging from 380 nm through 410 nm and dividing this by the integration (sum) of absorbance from wavelengths ranging from 340 nm through 350 nm.

According to certain embodiments of the invention, the LSAR of particulate metal oxides of the present invention is greater than the Long-Short Absorbance Ratio of a comparable particulate metal oxide. As used herein, "comparable particulate metal oxide" means a metal oxide the contains substantially the same weight percentage of zinc cation portion as the inventive particulate metal oxide, but which does not comprise both the manganese dopant portion and second dopant portion selected from the group consisting of iron and aluminum. For example, if the cationic portion of the inventive particulate metal oxide includes iron (such as about 0.1% by weight or more), then the comparable particulate metal oxide will not include manganese or aluminum dopant. If the cationic portion of the inventive particulate metal oxide does not include iron (such as about 0.1% by weight of iron or less), then the comparable particulate metal oxide has its aluminum replaced with manganese. These particular comparable compositions are selected as described above to provide high LSAR, since, as described in the examples below, zinc-oxide doped with only Fe generally has higher LSAR than zinc oxide doped with only Mn, which has a higher LSAR than zinc oxide doped with only Al.

The following examples are illustrative of the principles and practice of this invention, although not limited thereto. Numerous additional embodiments within the scope and spirit of the invention will become apparent to those skilled in the art once having the benefit of this disclosure.

EXAMPLES

Example IA

Preparation of Inventive Examples

Inventive Example E1

Zinc oxide containing both iron and manganese dopant portions was prepared by a sol-gel process utilizing zinc acetate dehydrate and iron (II) chloride hexahydrate. In a 100-ml beaker, 20 ml distilled water and 30 ml triethanolamine were combined and 2 ml of ethanol was added dropwise with continuous stirring until a visibly homogeneous solution was obtained. In another beaker, 0.5M iron (II) chloride hexahydrate was prepared (6.78 g iron chloride in 50 mL water). In a third beaker, 0.5M zinc acetate dihydrate was prepared. In another beaker, 0.5M of manganese (II) chloride was prepared. The solutions were allowed to continue to stir for 2-3 hours. In a 500-ml beaker the TEA/water mixture as well as the zinc acetate solution and iron (II) chloride solution were mixed. Sufficient iron (II) chloride solution was added to provide 0.475% by weight of iron cations relative to the total cationic portion (zinc plus iron plus manganese). Similarly, sufficient manganese (II) chloride solution was added to provide 0.475% of manganese cations relative to the total cationic portion. Accordingly, the total amount of added dopant was 0.95% percent by weight of combined iron and manganese cations relative to the total cationic portion.

Six milliliters of ammonium hydroxide (28% to 30% active) was added with continuous heating at a temperature of about 45° C. to 50° C., with stirring for 20 minutes. About 10 ml of distilled water was added during this stirring step. This solution was allowed to sit for thirty minutes and a white bulky solution formed. This was washed 8-10 times with distilled water and filtered on a filter paper. The residue obtained was put in an oven for drying at about 60° C. for 12 hours. The yellow/white powder obtained was subjected to calcinations at 700° C. for 4 hours. After calcination, the material was ground with a ceramic mortar and pestle. The resulting powder was mixed with petrolatum to a concentration of 5% powder by mass.

Inventive Example E2-E3

Zinc oxide doped with both iron and manganese was prepared by a sol-gel process utilizing zinc acetate dehydrate, iron (II) chloride hexahydrate, and manganese (II) chloride similarly to Inventive Example E1. For Inventive Example E2, sufficient iron (II) chloride solution was added to provide 0.7125% by weight of iron cations relative to the total cationic portion (zinc plus iron plus manganese). Sufficient manganese (II) chloride solution was added to provide 0.2375% of manganese cations relative to the total cationic portion. Accordingly, the total amount of added dopant was 0.95% percent by weight of combined iron and manganese cations relative to the total cationic portion, and the ratio of added iron cations to manganese cations was 3:1. For Inventive Example E3, sufficient iron (II) chloride solution was added to provide 0.2375% by weight of iron cations relative to the total cationic portion (zinc plus iron plus manganese). Sufficient manganese (II) chloride solution was added to provide 0.7125% of manganese cations relative to the total cationic portion. Accordingly, the total amount of added dopant was 0.95% percent by weight of combined iron and manganese cations relative to the total cationic portion, and the ratio of added iron cations to manganese cations was 1:3.

Inventive Example E4-E6

Zinc oxide doped with both aluminum and manganese was prepared by a sol-gel process utilizing zinc acetate dehydrate, aluminum (III) chloride, and manganese (II) chloride. Aside from substituting aluminum (III) chloride for iron (II) chloride, the method was similar to Inventive Examples E1-E3. For Inventive Example E4, sufficient aluminum (III) chloride solution was added to provide 0.7125% by weight of aluminum cations relative to the total cationic portion (zinc plus aluminum plus manganese). Sufficient manganese (II) chloride solution was added to provide 0.235% of manganese cations relative to the total cationic portion. Accordingly, the total amount of added dopant was 0.95% percent by weight of combined aluminum and manganese cations relative to the total cationic portion, and the ratio of added aluminum cations to manganese cations was 3:1. For Inventive Example E5, sufficient aluminum (III) chloride solution was added to provide 0.475% by weight of aluminum cations relative to the total cationic portion (zinc plus iron plus manganese). Sufficient manganese (II) chloride solution was added to provide 0.475% of manganese cations relative to the total cationic portion. Accordingly, the total amount of added dopant was 0.95% percent by weight of combined aluminum and manganese cations relative to the total cationic portion, and the ratio of added aluminum cations to manganese cations was 1:1. For Inventive Example E6, sufficient aluminum (III) chloride solution was added to provide 0.2375% by weight of aluminum cations relative to the total cationic portion (zinc plus aluminum plus manganese). Sufficient manganese (II) chloride solution was added to provide 0.7125% of manganese cations relative to the total cationic portion. Accordingly, the total amount of added dopant was 0.95% percent by weight of combined aluminum and manganese cations relative to the total cationic portion, and the ratio of added aluminum cations to manganese cations was 1:3.

Inventive Example E7

Zinc oxide doped with iron, aluminum and manganese was prepared by a sol-gel process utilizing zinc acetate dehydrate, iron (II) chloride hexahydrate, aluminum (III) chloride, and manganese (II) chloride. Aside from adding the additional source of cations, the method was similar to Inventive Examples E1-E6. Sufficient aluminum (III) chloride solution was added to provide 0.2375% by weight of aluminum cations relative to the total cationic portion (zinc plus aluminum plus iron plus manganese). Sufficient iron (II) chloride solution was added to provide 0.2375% of iron cations relative to the total cationic portion. Sufficient manganese (II) chloride solution was added to provide 0.475% of manganese cations relative to the total cationic portion. Accordingly, the total amount of added dopant was 0.95% percent by weight of combined aluminum, iron, and manganese cations relative to the total cationic portion. The ratio of added aluminum cations to iron cations to manganese cations was 1:1:2 or, stated differently, a Al plus Fe:Mn ratio of 1:1.

Comparative Example C1

Fe-doped zinc oxide was prepared by a sol-gel process utilizing zinc acetate dehydrate and iron (II) chloride hexahydrate in a manner similar to Inventive Examples E1-E3, except that manganese (II) chloride was omitted, while maintaining the total amount of added dopant at 0.95% by weight. Sufficient iron (II) chloride solution was added to provide 0.95% by weight of iron cations relative to the total cationic portion (iron plus zinc). Accordingly, the total amount of added dopant was 0.95% percent by weight of iron cations relative to the total cationic portion.

Comparative Example C2

Mn-doped zinc oxide was prepared by a sol-gel process in a manner similar to that described above for Comparative Example C1, except that manganese (II) chloride was used in place of iron (II) chloride hexahydrate. Sufficient manganese (II) chloride solution was added to provide 0.95% of manganese relative to the total cationic portion (zinc plus manganese). Accordingly, the total amount of added dopant was 0.95% percent by weight of manganese cations relative to the total cationic portion.

Comparative Example C3

Al-doped zinc oxide was prepared by a sol-gel process in a manner similar to that described above for Comparative Examples C1-C2, except that aluminum (III) chloride was used. Sufficient aluminum (III) chloride solution was added to provide 0.95% of aluminum cations relative to the total cationic portion (zinc plus aluminum). Accordingly, the total amount of added dopant was 0.95% percent by weight of aluminum cations relative to the total cationic portion.

Comparative Example C4

Undoped zinc oxide was prepared by a sol-gel process in a manner similar to that described above, except that only zinc acetate dehydrate was used, with no dopants (i.e., no aluminum, iron, or manganese salts).

Example IB

Spectrophotometric Analysis of Zinc Oxide Samples

Comparative Examples C1, C2, C3, and C4 and Inventive Examples E1-E7 were separately dispersed to a concentration by weight of 5% in petrolatum. Furthermore, a commercially available zinc oxide, Z-Cote HP1, commercially available from BASF of Ludwigshafen, Germany, was also dispersed in petrolatum (reported as Comparative Example C5). Each of these test samples were evaluated for UV-absorbance spectrum on Vitro-Skin (available from Innovative Measurement Solutions of Milford, Conn.) using a Labsphere 100UV spectrophotometer (Labsphere, North Sutton, N.H., USA).

The test material was evenly applied over the Vitro-Skin at 2 mg/cm$^2$ and compared with untreated Vitro-Skin. Absorbance was measured using a calibrated Labsphere UV-1000S UV transmission analyzer (Labsphere, North Sutton, N.H., USA). This was performed in duplicate for each batch of synthesized sample.

From the absorbance measurements, the relative amount of absorbance in the long wavelength UVA-I and visible region of the spectrum (the region of the spectrum that is typically absorbed less by conventional sunscreens, yet is still responsible for biological deleterious effects) as compared with short wavelength UVA I absorbance was determined. This ratio of absorbance across long wavelengths to absorbance at shorter wavelengths thus provides a basis for comparing the ability of the various doped particulate zinc oxides to absorb in this region of the spectrum. Specifically, a "Long-Short Absorbance Ratio" (LSAR) was determined for each sample by integrating (summing) the absorbance from wavelengths ranging from 380 nm through 410 nm and dividing this by the integration (sum) of absorbance from wavelengths ranging from 340 nm through 350 nm. The mean Long-Short Absorbance Ratio is reported, and where doped zinc oxide synthesis was conducted in triplicate, standard deviation is also reported as a non-zero value.

As a standard of comparison, an "Expected Value" for Long-Short Absorbance Ratio ($LSAR_{expected}$) is also reported in Table I. The Expected Value is calculated assuming a (linear) weighted average of the absorbance of each of the component dopants. For example, the Expected Value for Inventive Example E2, since it is Fe:Mn, 3:1 would be $$LSAR_{expected} = [(\tfrac{3}{4}) \times LSAR_{measured, Fe}] + [(\tfrac{1}{4}) \times LSAR_{measured, Mn}] = [(\tfrac{3}{4}) \times 1.67] + [(\tfrac{1}{4}) \times 1.53] = 1.63$$

The results for doped zinc oxide samples are shown in Table 1. Similarly, the results for undoped zinc oxide samples and commercially available Z-Cote HP1 are shown in Table 2.

TABLE 1

| TABLE 1: Example | Cations | Cation Ratio | $LSAR_{measured}$ Mean/ Std Dev. (Measured) | $LSAR_{expected}$ Expected Value (Calculated) | Percent Difference (Calculated) |
|---|---|---|---|---|---|
| Comparative Example C1 | Fe | — | 1.67/0.049 | — | — |
| Comparative Example C2 | Mn | — | 1.53/0.064 | — | — |
| Inventive Example E2 | Fe:Mn | 3:1 | 1.84 | 1.63 | 12.9% |
| Inventive Example E1 | Fe:Mn | 1:1 | 1.82/0.050 | 1.60 | 13.8% |
| Inventive Example E3 | Fe:Mn | 1:3 | 1.80 | 1.56 | 15.3% |
| Comparative Example C3 | Al | — | 1.42 | — | — |
| Comparative Example C2 | Mn | — | 1.53/0.064 | — | — |
| Inventive Example E4 | Al:Mn | 3:1 | 1.67 | 1.45 | 15.1% |
| Inventive Example E5 | Al:Mn | 1:1 | 1.77/0.035 | 1.47 | 20.4% |
| Inventive Example E6 | Al:Mn | 1:3 | 1.63 | 1.50 | 8.67% |
| Inventive Example E7 | Al:Fe:Mn | 1:1:2 | 1.84 | 1.53 | 20.2% |

TABLE 2

Long-Short Absorbance Ratios of Undoped Zinc Oxide and Z-COTE HP-1

| Example | Cations | $LSAR_{measured}$ Mean/ Std Dev. (Measured) |
|---|---|---|
| Comparative Example C4 | Zinc only | 1.46 |
| Comparative Example C5 (Z-COTE HP-1) | Zinc | 0.87 |

As shown in Tables 1 and 2 above, the inventive examples are metal oxides having a cationic portion that is more than 99% zinc and further including magnesium ion dopant and a second dopant selected from iron and/or aluminum. As shown, the manganese dopant portion and the second dopant portion are present in a ratio from 1:3 to 3:1.

It is particularly surprising that in each case, when two dopants were used, the Long-Short Absorbance Ratio was higher than a comparable metal oxide having either of the two components dopants alone. For example, Fe-doped, Comparative Example C1 has a higher Long-Short Absorbance Ratio than Mn-doped, Comparative Example C2. Rather than having a Long-Short Absorbance Ratio that is a "blend" between the two, such as given by the (expected) weighted average, Inventive Examples E1-E3 have a Long-Short Absorbance Ratio that is considerably (12.9% to 15.3%) higher than the expected value. Even more surprising, Inventive Examples E1-E3 have a Long-Short Absorbance Ratio that is actually higher than the larger of Comparative Examples C1 and C2.

Similarly, when three dopants were used, e.g. manganese, iron and aluminum, the Long-Short Absorbance Ratio was higher than when using any of the three component dopants alone.

The invention claimed is:

1. A particulate metal oxide comprising a cationic portion, wherein the cationic portion comprises about 99% by weight or more of a zinc portion, a first manganese dopant portion and a second dopant portion selected from the group consisting of iron and aluminum, wherein the first manganese dopant portion and the second dopant portion are present in a weight ratio from about 1:5 to about 5:1.

2. The particulate metal oxide of claim 1 having a Long-Short Absorbance Ratio that is greater than a Long-Short Absorbance Ratio of a comparable particulate metal oxide.

3. The particulate metal oxide of claim 1, wherein the first manganese dopant portion and the second dopant portion are present in a weight ratio from 1:4 to about 4:1.

4. The particulate metal oxide of claim 1, wherein the first manganese portion and the second dopant portion are present in a weight ratio from 1:3 to about 3:1.

5. The particulate metal oxide of claim 1 wherein the second dopant portion is iron.

6. The particulate metal oxide of claim 1 wherein the second dopant portion is aluminum.

7. The particulate metal oxide of claim 1 wherein the first manganese dopant portion is divalent.

8. The particulate metal oxide of claim 1 wherein the first manganese dopant portion is divalent and the iron dopant is divalent.

9. The particulate metal oxide of claim 1 having a Long-Short Absorbance Ratio of 1.75 or greater.

10. The particulate metal oxide of claim 1 having a Long-Short Absorbance Ratio of 1.80 or greater.

11. The particulate metal oxide of claim 1, wherein the cationic portion consists essentially of the zinc portion, the first manganese dopant portion and the second dopant portion.

12. The particulate metal oxide of claim 1 wherein the first manganese dopant portion is divalent and the second dopant portion consists essentially of a divalent iron dopant and a trivalent aluminum dopant, wherein the first manganese portion, the iron dopant and the aluminum dopant are present in a weight ratio of 1:1:2.

13. A sunscreen composition comprising a cosmetically acceptable carrier and the particulate metal oxide of claim 1.

* * * * *